US011224495B2

(12) United States Patent
Reinke et al.

(10) Patent No.: US 11,224,495 B2
(45) Date of Patent: Jan. 18, 2022

(54) MEDICAL DEVICE SUPPORT SYSTEM

(71) Applicant: Welch Allyn, Inc., Skaneateles Falls, NY (US)

(72) Inventors: Christian H. Reinke, York, SC (US);
Carlos Suarez, Syracuse, NY (US);
Richard M. Farchione, Fayetteville, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 16/890,448

(22) Filed: Jun. 2, 2020

(65) Prior Publication Data

US 2020/0383749 A1 Dec. 10, 2020

Related U.S. Application Data

(60) Provisional application No. 62/858,947, filed on Jun. 7, 2019.

(51) Int. Cl.
| *F16M 13/02* | (2006.01) |
| *A61B 90/50* | (2016.01) |
| *F16C 11/10* | (2006.01) |
| *F16H 21/44* | (2006.01) |
| *A61B 90/00* | (2016.01) |

(52) U.S. Cl.
CPC .............. *A61B 90/50* (2016.02); *F16C 11/10* (2013.01); *F16H 21/44* (2013.01); *F16M 13/022* (2013.01); *A61B 90/37* (2016.02); *F16M 2200/06* (2013.01)

(58) Field of Classification Search
CPC combination set(s) only.
See application file for complete search history.

(56) References Cited

U.S. PATENT DOCUMENTS

| 4,116,548 A | 9/1978 | Persson | |
| 7,289,315 B2 * | 10/2007 | Hillman | ................. F16M 11/10 |
| | | | 248/280.11 |

(Continued)

FOREIGN PATENT DOCUMENTS

| EP | 3275394 | 1/2018 |
| WO | WO2016145178 | 9/2016 |

(Continued)

OTHER PUBLICATIONS

Extended European Search Report dated Oct. 28, 2020 for European Patent Application No. 20178340.4, 12 pages.

*Primary Examiner* — Monica E Millner
(74) *Attorney, Agent, or Firm* — Lee & Hayes, P.C.

(57) ABSTRACT

A system includes a base, and an actuator having a first end and a second end. The system also includes a shaft configured to rotate relative to the base, and a drive link fixed to the shaft. The system further includes a support arm. A first end of the support arm being fixed to the shaft such that rotation of the shaft causes commensurate rotation of the support arm. The system also includes a timing link having a first end pivotably connected to the base and a second end opposite the first end. Additionally, the system includes a mount coupled to the second end of the timing link. The mount is configured to maintain a substantially constant orientation relative to the base as the support arm transitions between a raised position and a lowered position.

20 Claims, 9 Drawing Sheets

(56) References Cited

U.S. PATENT DOCUMENTS

| | | | |
|---|---|---|---|
| 7,597,298 B2 | 10/2009 | Papendieck et al. | |
| 9,243,743 B2 * | 1/2016 | Hunter | F16M 11/048 |
| 9,888,766 B2 * | 2/2018 | Chuang | F16M 11/2092 |
| 10,413,327 B2 * | 9/2019 | Ahluwalia | A61B 90/50 |
| 10,760,731 B2 * | 9/2020 | Chang | F16F 9/54 |
| 2004/0084587 A1 * | 5/2004 | Oddsen | F16M 11/2014 |
| | | | 248/284.1 |
| 2007/0108355 A1 * | 5/2007 | Li | F16M 11/08 |
| | | | 248/280.11 |
| 2007/0187562 A1 * | 8/2007 | Gaida | F16M 13/027 |
| | | | 248/280.11 |
| 2014/0246552 A1 | 9/2014 | Hunter et al. | |
| 2018/0028387 A1 * | 2/2018 | Yellin | A61B 90/50 |
| 2019/0086022 A1 * | 3/2019 | Anderson | F16M 11/2014 |
| 2019/0125485 A1 * | 5/2019 | Usui | A61B 34/32 |

FOREIGN PATENT DOCUMENTS

| | | |
|---|---|---|
| WO | WO2016160272 | 10/2016 |
| WO | WO2018132386 | 7/2018 |

\* cited by examiner

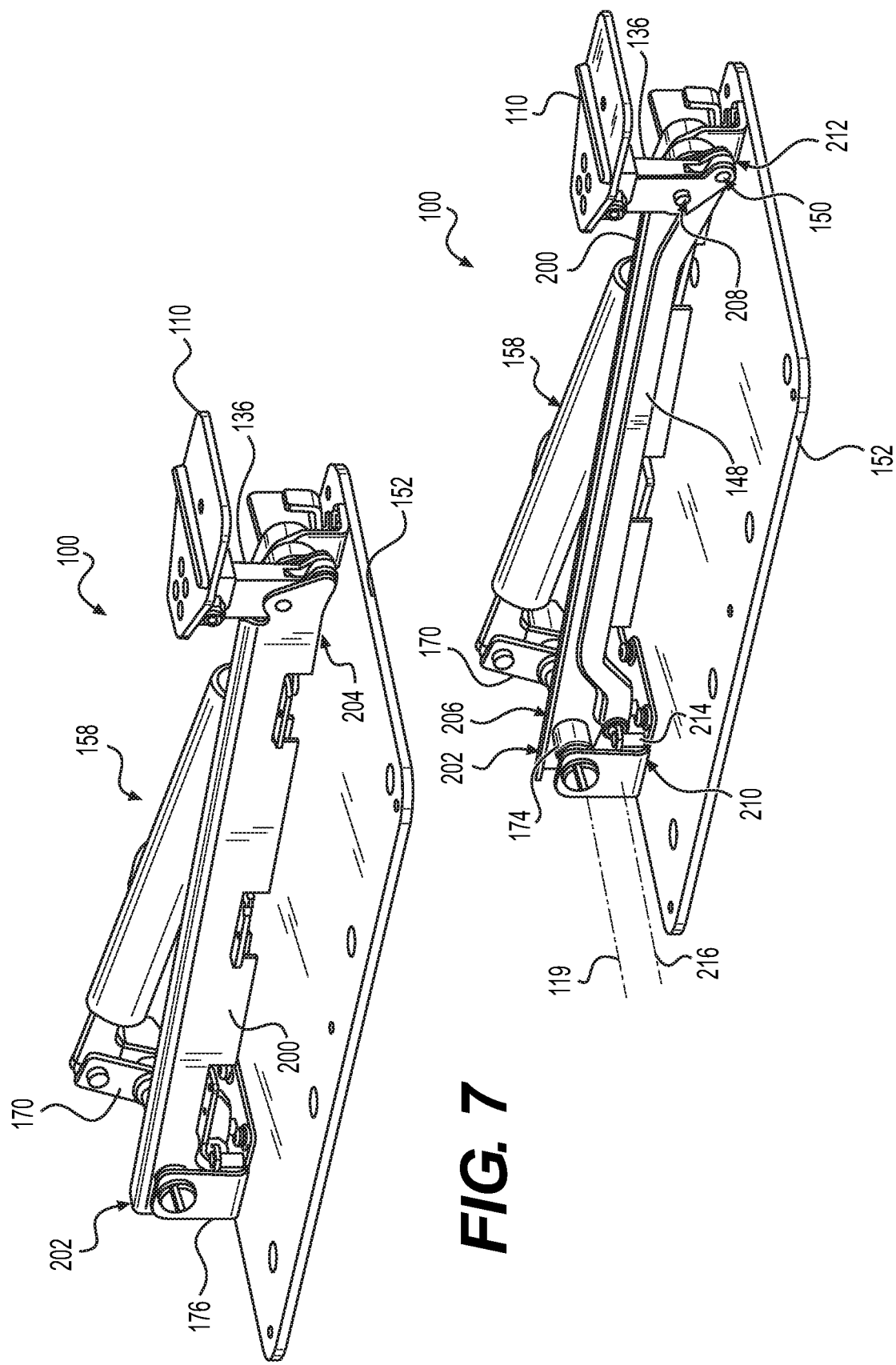

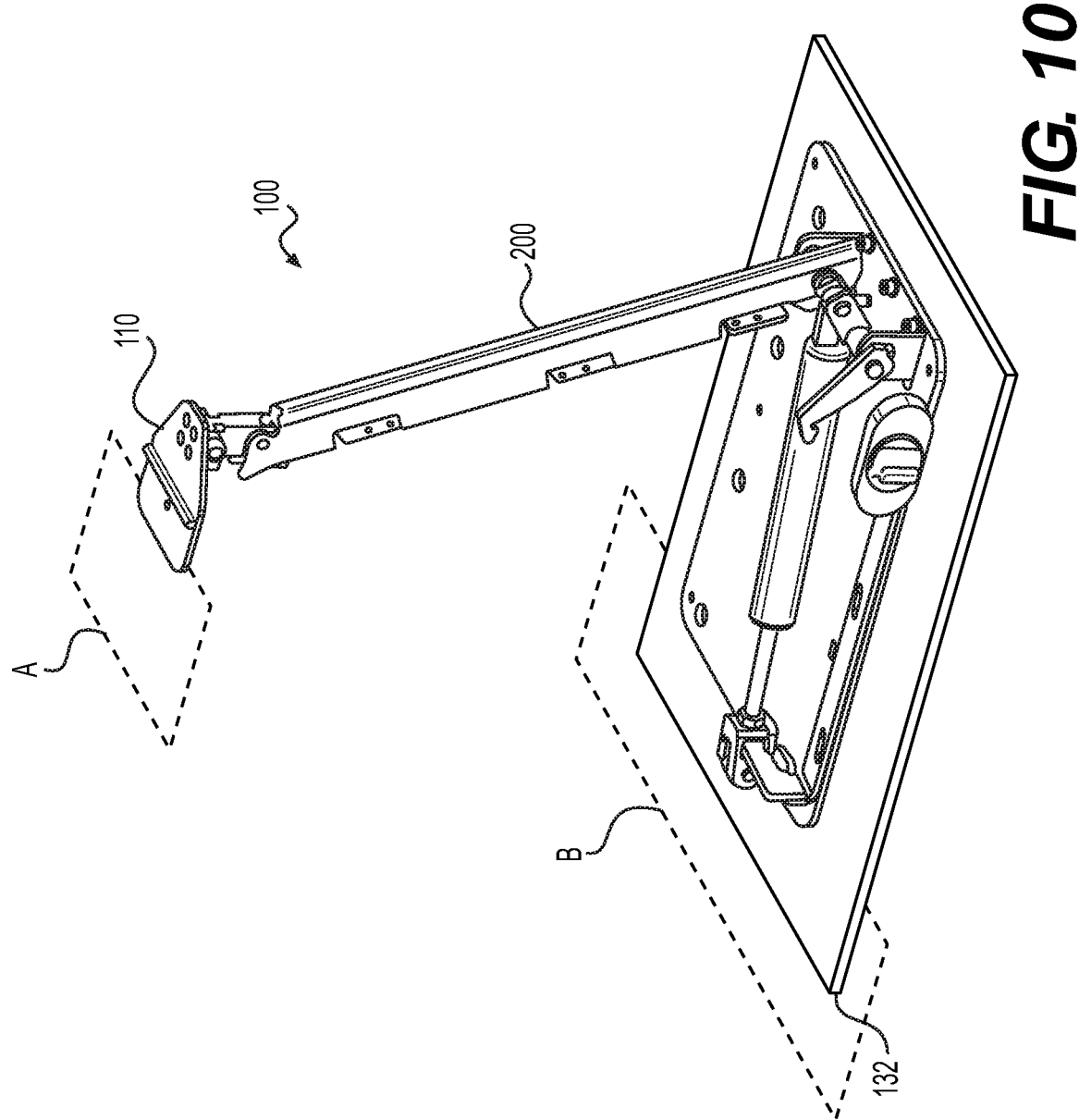

MEDICAL DEVICE SUPPORT SYSTEM

CROSS-REFERENCE TO RELATED APPLICATION

This application is a nonprovisional of, and claims priority to, U.S. Provisional Patent Application No. 62/858,947, filed on Jun. 7, 2019, the entire disclosure of which is incorporated herein by reference.

FIELD OF THE INVENTION

The present disclosure relates to systems and methods for supporting one or more medical devices and, in particular, to systems and methods configured to raise and lower medical devices while maintaining the orientation of such medical devices substantially constant relative to, for example, a stationary component of the system.

BACKGROUND OF THE INVENTION

Holding a medical device, such as a retina screener, can be tiring and cumbersome over long periods of time. Existing medical device pedestals do not enable healthcare practitioners to easily raise and lower the medical device in order to appropriately position the device. Such pedestals also to not include a locking mechanism that makes it easy for the practitioner to close and/or transport the pedestal in a convenient way.

The example embodiments of the present disclosure are directed toward overcoming the deficiencies described above.

SUMMARY

Example embodiments of the present disclosure relate to system for supporting a retinal camera or other like medical device. As will be described in greater detail below, in some examples, the system includes a base and an actuator pivotably mounted to the base at a first end. The second end of the actuator is coupled to a linkage that is fixedly coupled to a rotatable shaft. Through this configuration, the actuator may act on the linkage to cause commensurate rotation of both the linkage and the rotatable shaft about, for example, a longitudinal axis of the shaft.

In such examples, the system also includes a support arm coupled to the rotatable shaft, and a timing link having a first end pivotably connected to the base and a second end coupled to the support arm. A mount is supported by the second end of the timing link. Through this configuration, rotation of the rotatable shaft causes commensurate rotation of the support arm and also drives rotation of the timing link. Additionally, the mount is configured to maintain a substantially constant angular position (e.g., remain substantially parallel) relative to the base as the support arm rotates relative to the base. The system further includes a locking mechanism configured to fix the position of the gas cylinder (and thus, the position of the support arm) at various locations along the range of travel of the arm.

In an example embodiment, a system includes a substantially planar base, and a gas cylinder configured to transition between an extended state and a retracted state, the gas cylinder having a first end connected to a bracket that is fixed relative to the base, and a second end pivotably connected to a drive link. The system also includes a shaft having a longitudinal axis, the shaft being supported by the base and configured to rotate, relative to the base, about the longitudinal axis, the drive link being fixed to the shaft such that movement of the drive link caused by transitioning of the gas cylinder between the extended state and the retracted state results in commensurate rotation of the shaft. The system further includes a support arm disposed opposite the drive link, the support arm having a first end and a second end, the first end of the support arm being fixed to the shaft such that rotation of the shaft causes commensurate rotation of the support arm. The system also includes a timing link having a first end pivotably connected to the base and a second end opposite the first end of the timing link. Additionally, the system includes a mount coupled to the second end of the timing link, the mount being configured to support the medical device and to maintain a substantially constant orientation relative to the base as the support arm transitions between a raised position relative to the base and a lowered position relative to the base.

In another example embodiment, a system includes a substantially rigid base, and an actuator connected to the base and configured to rotate a drive link about an axis. The system also includes a shaft configured to rotate about the axis, the drive link being fixed to the shaft such that movement of the drive link results in commensurate rotation of the shaft. The system further includes a support arm having a first end connected to the shaft, the support arm being rotatable about the axis, and a timing link having a first end pivotably connected to the base, and a second end disposed opposite the first end of the timing link. The system also includes a mount coupled to the second end of the timing link, the mount being configured to maintain a substantially constant orientation relative to the base as the support arm transitions between a raised position relative to the base and a lowered position relative to the base.

BRIEF DESCRIPTION OF THE DRAWINGS

FIG. 7 illustrates yet another view of the system shown in FIG. 1 with various outer components removed.

FIG. 8 illustrates still another view of the system shown in FIG. 1 with various outer components removed.

FIG. 10 illustrates yet another view of the system shown in FIG. 1 with various outer components removed.

DETAILED DESCRIPTION

Figure 1:
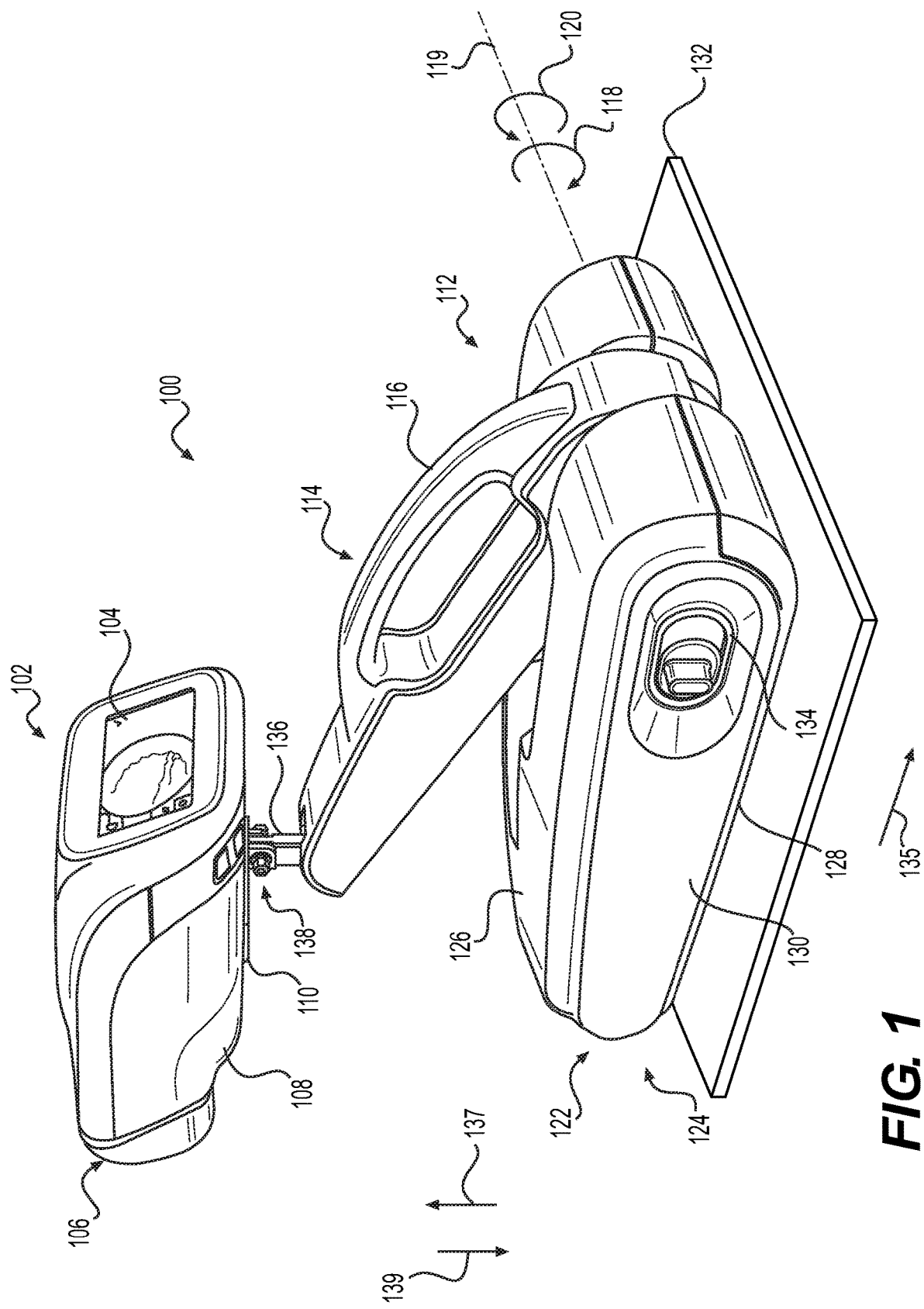
FIG. 1 illustrates a medical device support system, together with a medical device, according to an example embodiment of the present disclosure.

FIG. 1 illustrates an example system 100 of the present disclosure useful in, for example, supporting a medical device 102. Such a medical device 102 may include, for example, a hand-held retina scanner or other device used for vision screening or other patient care work flows. Whenever possible, like item numbers will be used throughout this disclosure to identify like components of the system 100.

Additionally, as will be described herein, implementation of the system 100 for supporting a medical device 102 is merely one example use of the system 100. The disclosed system 100 may be used and/or otherwise employed to support a variety of items other than the disclosed medical device 102 and/or other than medical devices, generally. Such additional uses will be apparent to one of ordinary skill in view of the present disclosure.

As shown in FIG. 1, the example system 100 may include, among other things, a mount 110 configured to support the medical device 102 as various components of the system 100 are raised, lowered, and/or otherwise moved relative to one another. In such examples, the mount 110 may comprise, for example, a substantially planar plate, platform, pedestal, and/or other structure configured to facilitate a removable connection between components of the system 100 and the medical device 102. As can be seen in FIG. 1, in some examples, the medical device 102 may include one or more components configured to assist healthcare professional and providing care to a patient. For example, in embodiments in which the medical device 102 comprises a hand-held retina scanner, or other similar device, the medical device 102 may include a first display 104 positioned at a first end thereof. The first display 104 may comprise, for example, a liquid crystal display, a capacitive touch screen display, and/or other display device configured to render one or more images viewable by the healthcare professional during a retina scan or other medical procedure. In such examples, the medical device 102 may also include a second display 106 positioned at a second end thereof. During such retina scans or other medical procedures, the second display 106 may be configured to render one or more images viewable by the patient. Additionally, in some examples, the second display 106 may include one or more sensors, cameras, and/or other imaging devices configured to capture reflected light, images, and/or other information during such medical procedures. It is understood that in further examples, the medical device 102 may include one or more such sensors, cameras, and/or other imaging devices that are separate from and/or in addition to the second display 106. In any of the examples described herein, the medical device 102 may include an outer housing or frame 108, and in such examples, the mount 110 may be configured to form a releasable connection with the frame 108 of the medical device 102. Such a connection may be formed by, for example, one or more screws, bolts, clips, brackets, and/or other components configured to connect the frame 108 of the medical device to the mount 110.

In any of the examples described herein, the system 100 may comprise an adjustable pedestal configured to support the medical device 102, and to maintain a substantially constant orientation of the medical device 102 relative to various stationary components of the system 100, as one or more additional movable components of the system 100 are transitioned between raised and lowered positions. As shown in FIG. 1, in such examples, the system 100 may include an outer housing 112. In any of the examples described herein, one or more portions of the outer housing 112 may be made from any substantially rigid material (e.g., plastics, polymers, metals, alloys, etc.) configured to assist in protecting various components of the system 100 encased within the housing 112. The outer housing 112 may include a first portion 114 that is rotatable, pivotable, and/or otherwise movable relative to other portions of the outer housing 112. For example, the first portion 114 of the outer housing 112 may include a handle 116 that is configured to be grasped by a health care professional or other user of the system 100. Grasping the handle 116, and rotating the handle 116 in the direction of arrow 118 about a rotational axis 119, may cause commensurate rotation of the first portion 114 of the outer housing 112 about the axis 119. Such rotation may also cause components of the system 100 to raise the mount 110 and/or the medical device 102 in the direction of arrow 137. Likewise, grasping the handle 116, and rotating the handle 116 in the direction of arrow 120 about the axis 119, may cause commensurate rotation of the first portion 114 about the axis 119. Such rotation may cause components of the system 100 to lower the mount 110 and/or the medical device 102 in the direction of arrow 139.

The outer housing 112 may also include a second portion, 122 that is configured to remain stationary relative to the first portion 114 as the first portion 114 is pivoted, rotated, raised, lowered, and/or otherwise moved throughout a range of motion of the first portion 114. For example, the second portion 122 may include a main body 124 comprising a top surface 126, a bottom surface 128 disposed opposite the top surface 126, and one or more sidewalls 130 extending from (and/or between) the top surface 126 to the bottom surface 128. In such examples, the second portion 122 of the housing 112 may be configured to rest on a support surface 132. As the first portion 114 of the outer housing 112 is pivoted, rotated, raised, lowered, and/or otherwise moved. For example, the bottom surface 128 of the second portion 122 may be supported by the support surface 132 during use of the system 100. In such examples, the bottom surface 128, and/or the second portion 122 of the outer housing 112 may remain substantially stationary relative to the support surface 132 as the first portion 114 of the outer housing 112 is moved (e.g., rotated) in order to position the medical device 102 at a desired location. Such a support surface 132 may comprise, for example, a table top, a desktop, a platform, a ground surface, and/or any other stationary surface or structure configured to support the entire weight of the system 100 and the medical device 102 during use.

As can be seen in FIG. 1, and as will be described in greater detail below, the system 100 may also include one or more controls that can be manipulated, moved, and/or otherwise utilized by a health care professional or other user of the system 100 in order to utilize various functions of the system 100. For example, the system 100 may include one or more tabs, buttons, levers, switches, and/or other controls 134. In the example illustrated in FIG. 1, the control 134 may comprise a button, lever, switch, tab, and/or other structure configured to activate, deactivate, and/or otherwise operate a locking mechanism of the system 100. For instance, as will be described in greater detail below, the control 134 may be movable in, for example, the direction of arrow 135 in order to disengage a latch or other component of the locking mechanism. Operating the control 134 in this way may, for example, cause an actuator of the system 100 to transition between a retracted state and an extended state, and such a transition may assist in, for example, rotating the first portion 114 of the outer housing 112 as described above.

As noted above, the mount 110 may be configured to support the medical device 102. The mount 110 may also be configured to maintain a substantially constant orientation relative to one or more stationary components of the system 100 and/or relative to the support surface 132 as the first portion 114 is rotated in either the direction of arrow 118 or the direction of arrow 120. As can be seen in FIG. 1, the system 100 may also include a stem 136 that is coupled to and/or otherwise connected to the mount 110 via a joint 138. It is understood that the mount 110, the stem 136, and/or any other components of the system 100 disposed substantially within the outer housing 112 may be made from any substantially rigid material, and such materials may include, for example, stainless steel, aluminum, titanium, and/or any other metals, alloys, plastics, polymers, and/or other like materials. Thus, the stem 136 may comprise a substantially rigid shaft, linkage, rod, and/or other such structure that is connected to the mount 110 at the joint 138, and that extends therefrom. For example, as will be described below, in some examples, the stem 136 may be connected to a timing link of the system 100 and, thus, may couple the mount 110 to the timing link. In any of the examples described herein, the joint 138 may comprise a substantially fixed joint, or a substantially movable joint. In any such examples, the joint 138 may comprise one or more screws, bolts, nuts, shafts, fittings, bearings, and/or any other components configured to fixedly or rotatably connect the mount 110, with the stem 136. Thus, it is understood that while the joint 138 may be described herein as maintaining the mount 110 at a fixed and/or substantially constant orientation relative to the stem 136, in other examples, the joint 138 may be configured to enable rotation of the mount 110 relative to the stem 136. For example, the joint 138 may include one or more compression washers, dampening hinges, and/or other such structures to facilitate fixing the mount 110 relative to the stem 136. Such structures may also allow for rotation of the mount 110 relative to the stem 136 in order to obtain a desired orientation of the mount 110 relative to the stem 136. Once such a desired orientation has been achieved, such structures may be tightened, locked, compressed, and/or otherwise configured to fix the orientation of the mount 110 relative to the stem 136.

Figure 2:
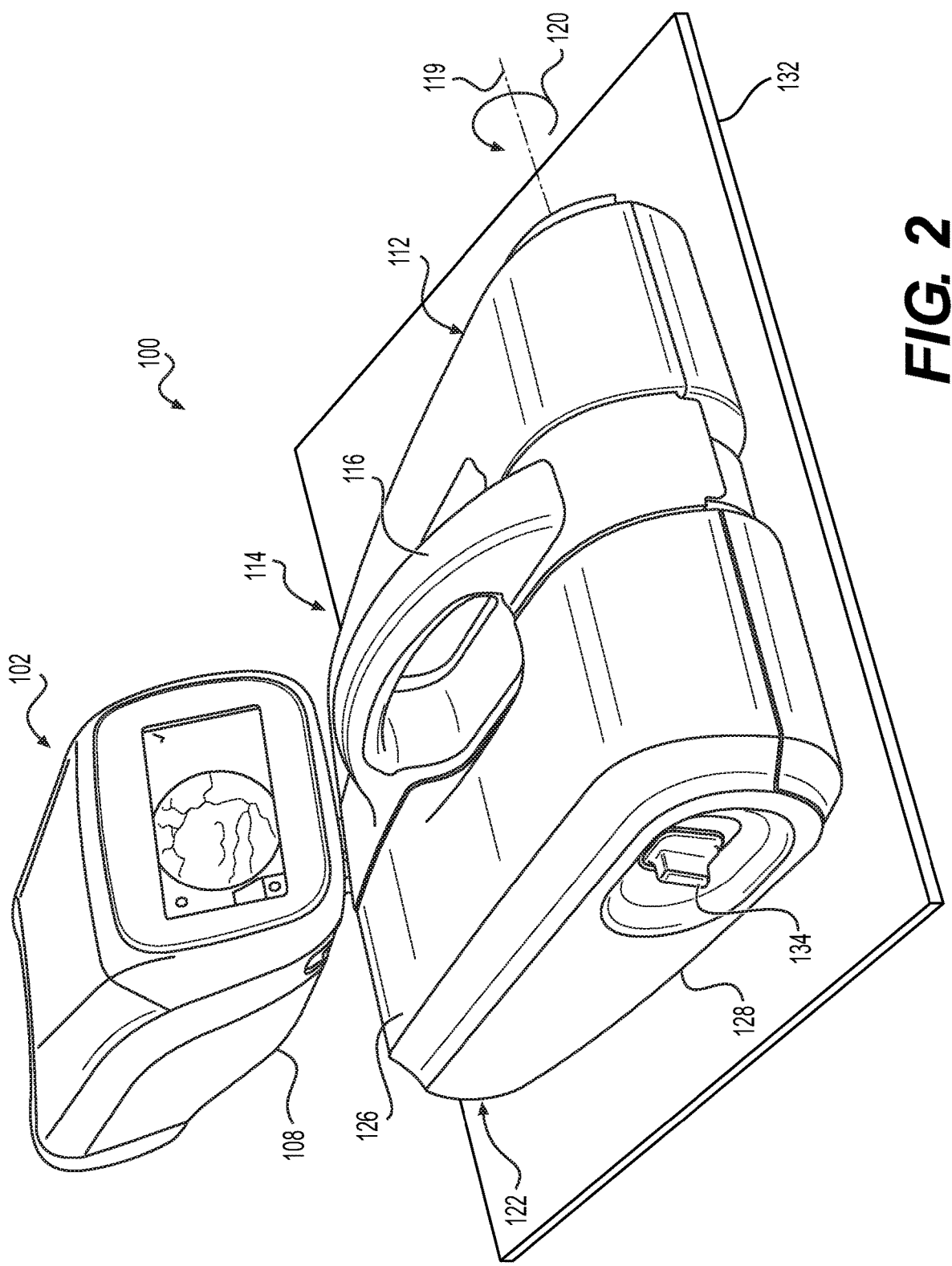
FIG. 2 illustrates another view of the system and medical device shown in FIG. 1.

FIG. 1 illustrates the first portion 114 of the housing 112 and/or the medical device 102 disposed in a substantially raised position in which the first portion 114 has been at least partially rotated in the direction of arrow 118 about the axis 119. FIG. 2, on the other hand, illustrates the first portion 114 and/or the medical device 102 disposed in a substantially lowered position in which the first portion 114 has been substantially completely rotated in the direction of arrow 120 about the axis 119. As can be seen from at least FIGS. 1 and 2, the mount 110 and/or other components of the system 100 cause the medical device 102 to maintain a substantially constant orientation relative to, for example, the second portion 122 of the outer housing 112 and/or relative to the support surface 132 as the first portion 114 transitions between the example raised position illustrated in FIG. 1 and the example lowered position illustrated in FIG. 2.

Figure 3:
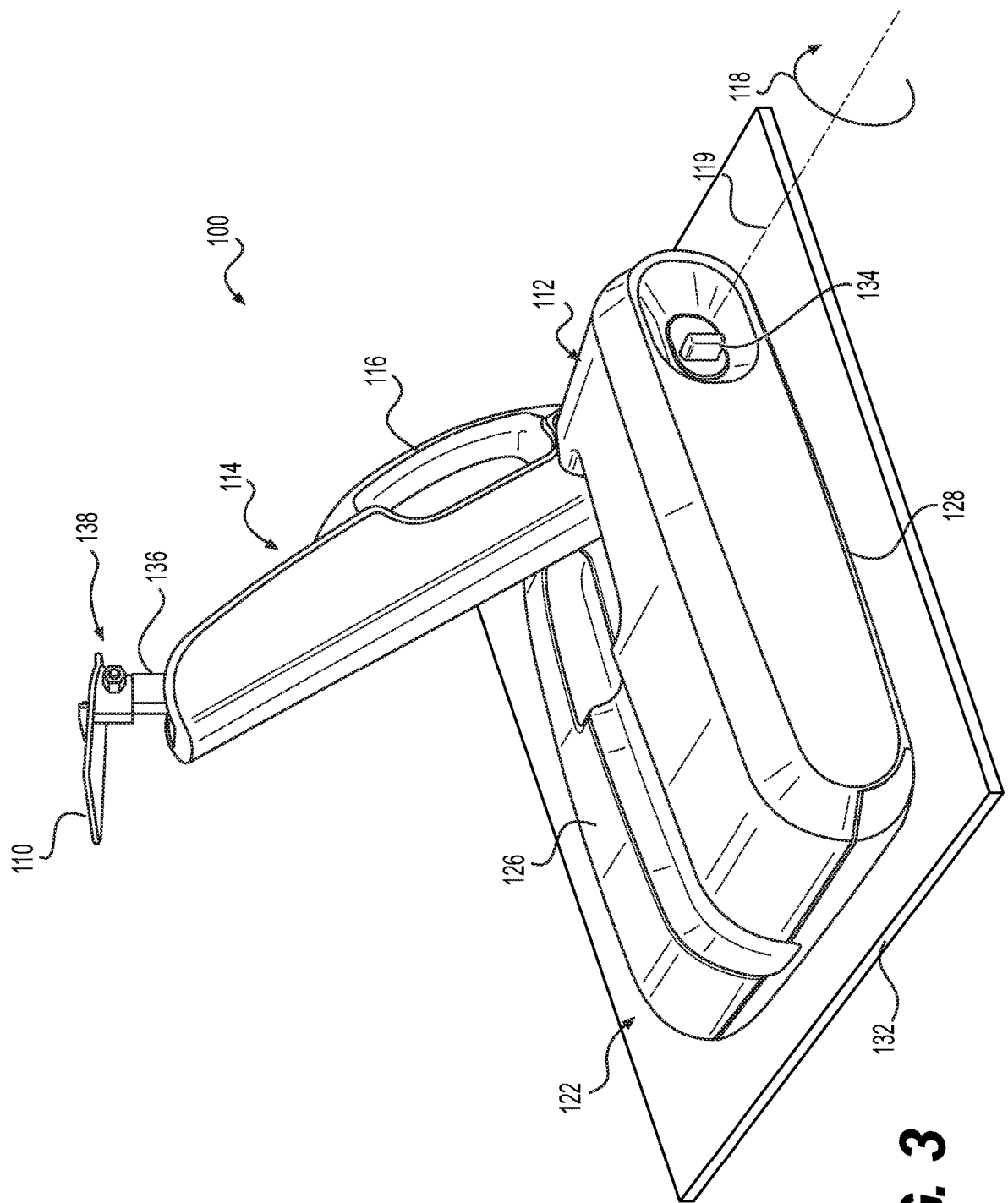
FIG. 3 illustrates a view of the system shown in FIG. 1 with the medical device removed.
Figure 4:
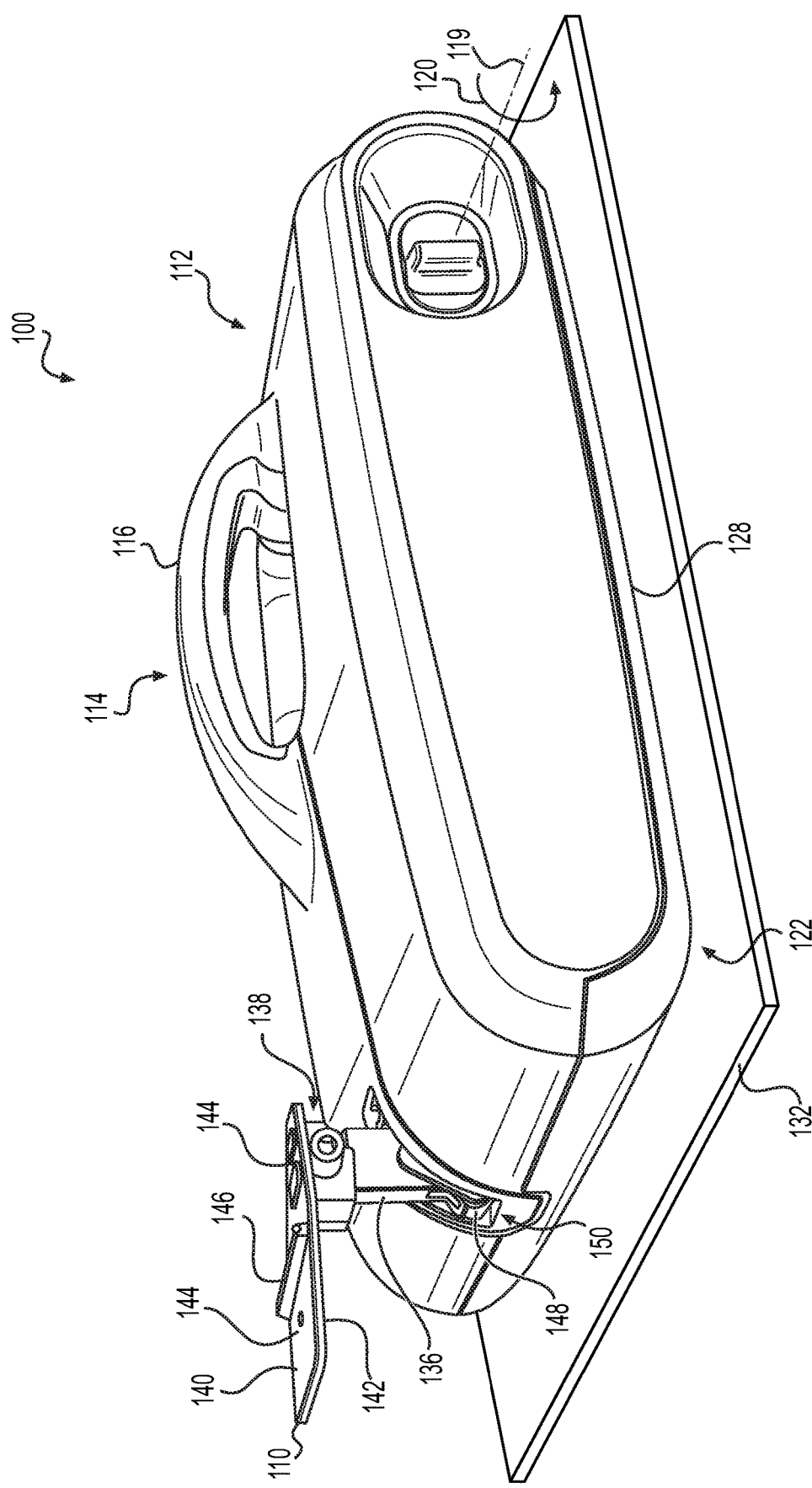
FIG. 4 illustrates another view of the system shown in FIG. 1 with the medical device removed.

FIG. 3 illustrates the first portion 114 of the housing 112 disposed in another example substantially raised position in which the first portion 114 has been at least partially rotated in the direction of arrow 118 about the axis 119. In FIG. 3, the medical device 102 has been removed from view for ease of description. FIG. 4 illustrates the first portion 114 disposed in another example substantially lowered position in which the first portion 114 has been substantially completely rotated in the direction of arrow 120 about the axis 119. As can be seen from at least FIGS. 3 and 4, the mount 110 of the system 100 is also configured to maintain a substantially constant orientation relative to, for example, the second portion 122 of the outer housing 112, stationary components of the system 100, and/or the support surface 132 as the first portion 114 transitions between the example raised position illustrated in FIG. 3 and the example lowered position illustrated in FIG. 4. As will be described in greater detail below, the connections between and/or other configurations of the stem 136, the timing link, and/or other components of the system 100 may assist the mount 110 and maintaining such a substantially constant orientation during use of the system 100.

As can be seen in at least FIG. 4, the mount 110 may include one or more components, structures, and/or other configurations configured to assist in removably connecting the medical device 102 (FIG. 1) to the mount 110. For example, the mount 110 may include a top surface 140, and a bottom surface 142 opposite the top surface 140. In such examples, the mount 110 may include one or more thru holes 104 and/or other like components configured to receive one or more bolts, screws, nuts, bearings, fasteners, clips, and/or other components configured to assist in releasably connecting the medical device 102 to the mount 110. Such through holes 104 may extend, for example, from the top surface 140 to the bottom surface 142. The mount 110 may also include one or more pledges, ribs, tabs, spines 146, grooves, extensions, and/or other components configured to assist with aligning the medical device 102, relative to the mount 110, and/or maintaining the releasable and/or removable connection between the medical device 102 and the mount 110. For example, such a spine 146 may comprise a ridge extending laterally upward from the top surface 140, and the spine 146 may be configured to mate with one or more corresponding channels formed by the frame 108 of the medical device 102 as the medical device 102 is positioned on to the top surface 140. The mating configuration between the spine 146 and the frame 108 of the medical device 102 may assist in laterally and/or transversely orientating medical device 102, relative to the mount 110.

FIG. 4 also illustrates a portion of the timing link 148 described above, as well as a joint 150 connecting the stem 136 with the timing link 148. As noted above, the stem 136 may be connected to the timing link 148, and thus, may couple the mount 110 to the timing link 148. In any of the examples described herein, the joint 138 may be substantially similar to the joint 138 described above. For example, the joint 150 may comprise a substantially fixed joint, or a substantially movable joint. In any such examples, the joint 150 may comprise one or more pins, screws, bolts, nuts, shafts, fittings, bearings, and/or any other components configured to fixedly or rotatably connect the stem 136 with the timing link 148. Thus, it is understood that while the joint 150 may be described herein as enabling rotation of the stem 136 relative to the timing link 148, in other examples, the joint 150 may maintain the stem 136 at a fixed and/or substantially constant orientation relative to the timing link 148.

Figure 5:
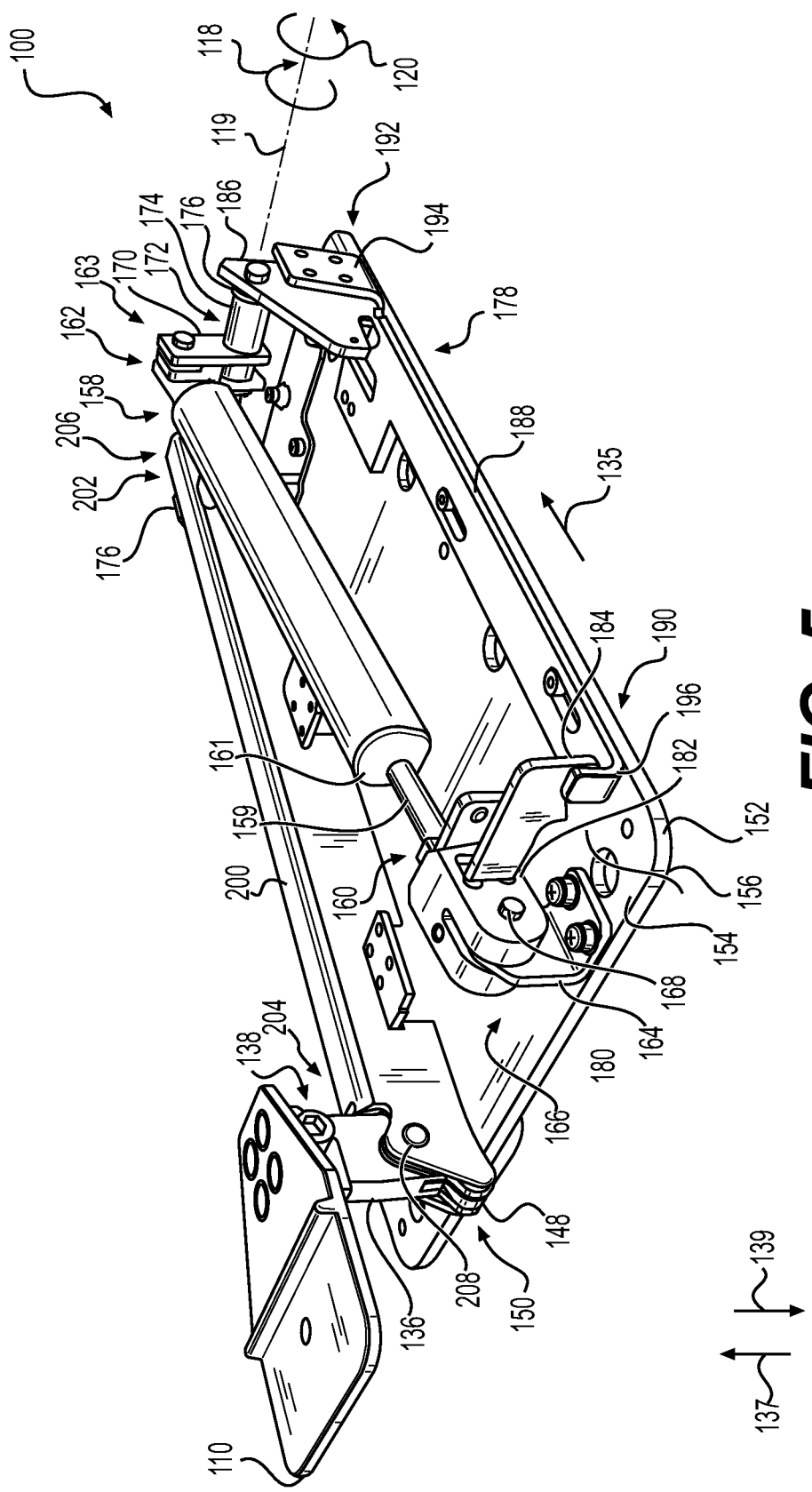
FIG. 5 illustrates the system of FIG. 1 with various outer components removed.

FIG. 5 illustrates various additional components of the system 100, and in FIG. 5, the outer housing 112 has been removed for ease of discussion. As shown in FIG. 5, the system 100 may include a substantially rigid base 152, and one or more components of the system 100 may be slidably, fixedly, rotatably, pivotably, movably, and/or otherwise connected to or supported by the base 152. In some examples, the base 152 may comprise a substantially planar base 152 of the system 100. For instance, the base 152 may include a top surface 154, and a bottom surface 156 opposite the top surface 154. In such examples, at least a portion of the top surface 154 may comprise a substantially planar surface, and/or at least a portion of the bottom surface 156 may comprise a substantially planar surface. The base 152 may be made from any of the metals, alloys, plastics, polymers, and/or other substantially rigid materials described herein, and the base 152 may be configured to support the entire weight of the system 100 and the medical device 102 when the system 100 is disposed on, for example, the support surface 132 described above with respect to FIG. 1.

Figure 9:
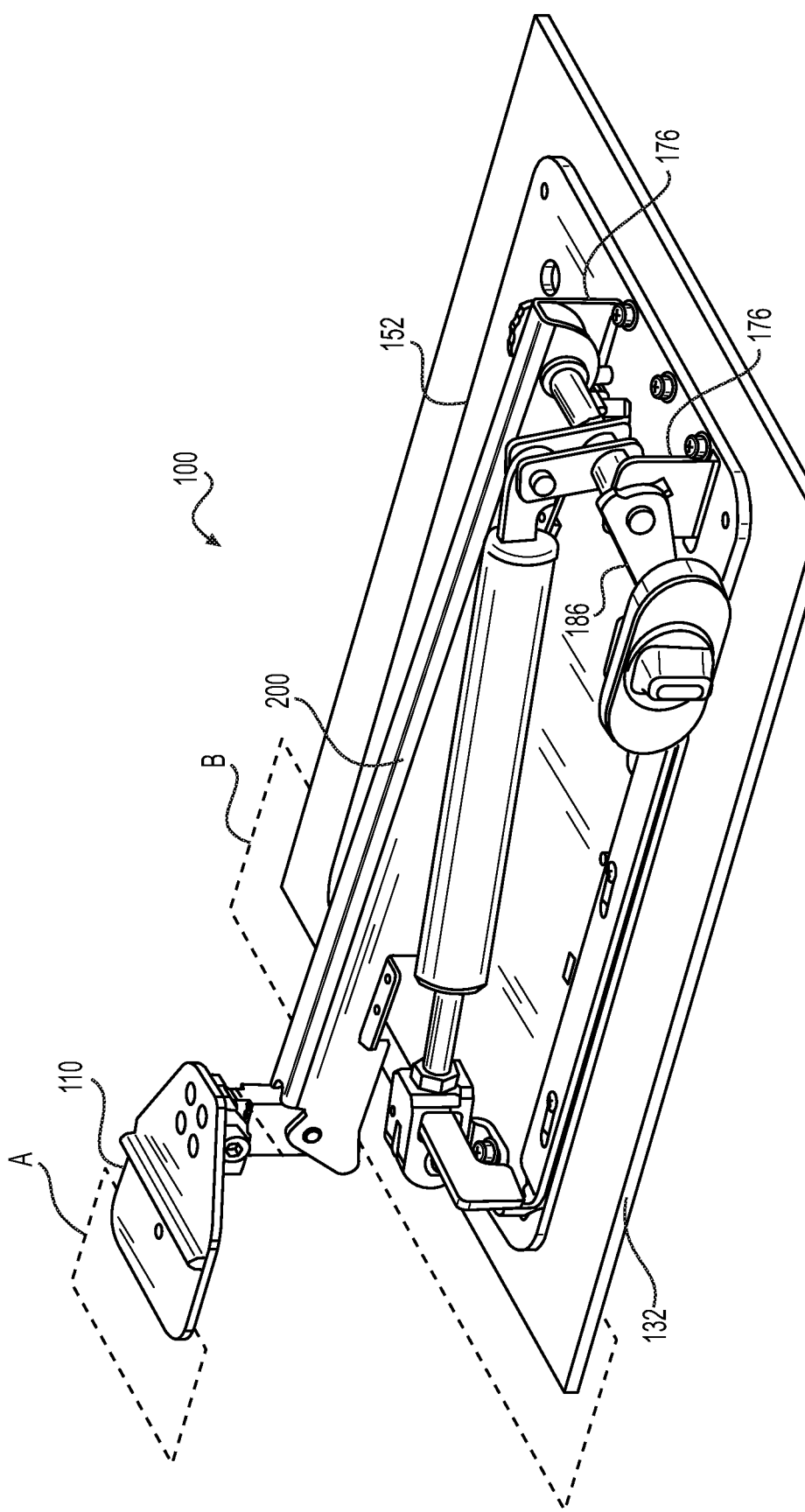
FIG. 9 illustrates a further view of the system shown in FIG. 1 with various outer components removed.

In any of the examples described herein, the system 100 may include one or more actuators 158 configured to assist in raising, lowering, rotating, pivoting, and/or otherwise moving one or more components of the system 100 relative to the base 152. For example, FIG. 5 illustrates an embodiment of the system 100 in which a single actuator 158 has been employed. However, in additional embodiments, two or more actuators 158, of the same type or of different types, may be included in the system 100 to assist in moving various components thereof. An example actuator 158 of the present disclosure may comprise, for example, a pressurized gas cylinder (e.g., a gas spring), a pneumatic actuator, an electromagnetic actuator (e.g., a solenoid), an electric actuator (e.g., a stepper motor), a mechanical actuator (e.g., a spring and shaft-based actuator), and/or any other device configured to direct a force and/or to cause movement of another object. Unless otherwise described herein, and for ease of description, the actuator 158 shown in FIG. 5 shall be described for the remainder of this disclosure as comprising a gas spring unless otherwise noted. In such examples, the actuator 158 may include a central cylinder 159 that is movably disposed within a pressurized housing 161. Such an example actuator 158 (e.g., a gas cylinder) may be configured to transition between an extended state in which the cylinder 159 extends at least partly from and/or at least partly outside of the housing 161, and retracted state in which the cylinder 159 is disposed at least partly and/or substantially entirely within the housing 161. It is understood that at least FIG. 5 and FIG. 9 illustrate the actuator 158 disposed in the retracted state, while at least FIG. 10 illustrates the actuator 158 in the extended state.

With continued reference to FIG. 5, the actuator 158 may include a first end 160, and a second end 162 opposite the first end 160. In such examples, the first end 160 may comprise a first end of the cylinder 159. In any of the examples described herein, the first end 160 of the actuator 158 may include one or more brackets, housings, fittings, and/or other structures configured to mate with one or more corresponding structures fixedly connected to the base 152. For example, as shown in FIG. 5, the actuator 158 may include a first end 160 that is connected to a bracket 164, and the bracket may be fixed relative to the base 152. For example, the bracket 164 may comprise a substantially rigid flange, plate, beam, piece of angle iron, wall, and/or other structure of the system 100 that is fixedly connected to the base 152. In such examples, the first end 160 of the actuator 158 may be fixedly, pivotably, rotatably, and/or otherwise connected to the bracket 164 via a joint 166. In any of the examples described herein, the joint 166 may be substantially similar to the joint 150 described above. For example, the joint 166 may comprise a substantially fixed joint, or a substantially movable joint. In any such examples, the joint 166 may comprise one or more pins, shafts, rods, screws, bolts, nuts, shafts, fittings, bearings, and/or any other components configured to fixedly or rotatably connect the first end 160 of the actuator 158 with the stationary bracket 164. Thus, it is understood that while the joint 166 may be described herein as enabling movement (e.g., partial rotation) of the first end 160 of the actuator 158 relative to the bracket 164, in other examples, the joint 166 may maintain the first end 160 of the actuator 158 at a fixed and/or substantially constant orientation relative to the bracket 164. In some examples, the joint 166 may include a central pin or shaft 168 extending through an orifice of the bracket 164 and extending at least partly through one or more components of the first end 160. In such examples, the first end 160 of the actuator 158 may be at least partly rotatable about a longitudinal axis (not shown) extending substantially centrally through the shaft 168.

As shown in FIG. 5, the second end 162 of the actuator 158 may be rotatably, pivotably, and/or otherwise movably connected to a drive link 170 of the system 100. Similar to the bracket 164 described above, the drive link 170 may comprise a substantially rigid flange, plate, beam, piece of angle iron, wall, and/or other structure of the system 100. In any of the examples described herein, the drive link 170 may be configured to receive a force applied by the second end 162 of the actuator 158, and to transfer at least part of the received force to another component of the system 100 that is connected to the drive link 170. For example, the second end 162 of the actuator 158 may be pivotably connected to the drive link 170, via a joint 163. In any of the examples described herein, the joint 163 may be substantially similar to the joint 150 described above. For example, the joint 163 may comprise a substantially fixed joint, or a substantially movable joint. In any such examples, the joint 163 may comprise one or more pins, shafts, rods, screws, bolts, nuts, shafts, fittings, bearings, and/or any other components configured to fixedly or rotatably connect the second end 162 of the actuator 158 with the drive link 170. For instance, as can be seen in FIG. 5, the joint 163 may include a central pin or shaft (similar to the shaft 168). In such examples, the shaft of the joint 163 may extend through an orifice of the drive link 170, and may extend at least partly through one or more components of the second end 162. In such examples, the second end 162 of the actuator 158 may be at least partly rotatable about a longitudinal axis (not shown) extending substantially centrally through the shaft of the joint 163.

In any of the examples described herein, the drive link 170 may be fixed to, mounted to, and/or otherwise connected to one or more additional components of the system 100 such that movement of the drive link 170 caused by transitioning of the actuator 158 between the extended state and the retracted state described above results in commensurate movement of such additional components. For example, the drive link 170 may be fixed to, mounted on, and/or otherwise connected to a shaft 174 of the system 100. For example, the drive link 170 may be connected to the shaft 174 via one or more joints 172. In any of the examples described herein, the joint 172 may be substantially similar to the joint 150 described above. For example, the joint 172 may comprise a substantially fixed joint, or a substantially movable joint. In any such examples, the joint 172 may comprise one or more pins, keys, teeth, fittings, bearings, and/or any other components configured to fixedly connect the drive link 170 to the shaft 174. Additionally, in some examples the axis 119 described above may comprise a central longitudinal axis of the shaft 174, and such an axis 119 may extend substantially centrally through the joint 172. Further, the system 100 may also include one or more brackets 176 configured to retain the shaft 174 during use. Such brackets 176 may be substantially similar to, for example, the bracket 164 described above. In particular, each bracket 176 may comprise a substantially rigid flange, plate, beam, piece of angle iron, wall, and/or other structure of the system 100 that is fixedly connected to the base 152.

In such examples, shaft 174 may be pivotably, rotatably, and/or otherwise connected to the bracket 176. Thus, in various examples, the shaft 174 may be supported by the base 152 via one or more of the brackets 176 described herein. Due to this configuration, the actuator 158 may direct and/or apply a force (e.g., a rotational force) to the drive link 170 as the actuator 158 transitions between the extended state and the retracted state described above. Such a force may cause rotation and/or other movement of the drive link 170 (e.g., rotation of the drive link about the axis 119). Additionally, due to the fixed arrangement between the drive link 170 and the shaft 174, movement of the drive link 170 caused by transitioning of the actuator 158 may result in commensurate rotation of the shaft 174 about the axis 119.

Figure 6:
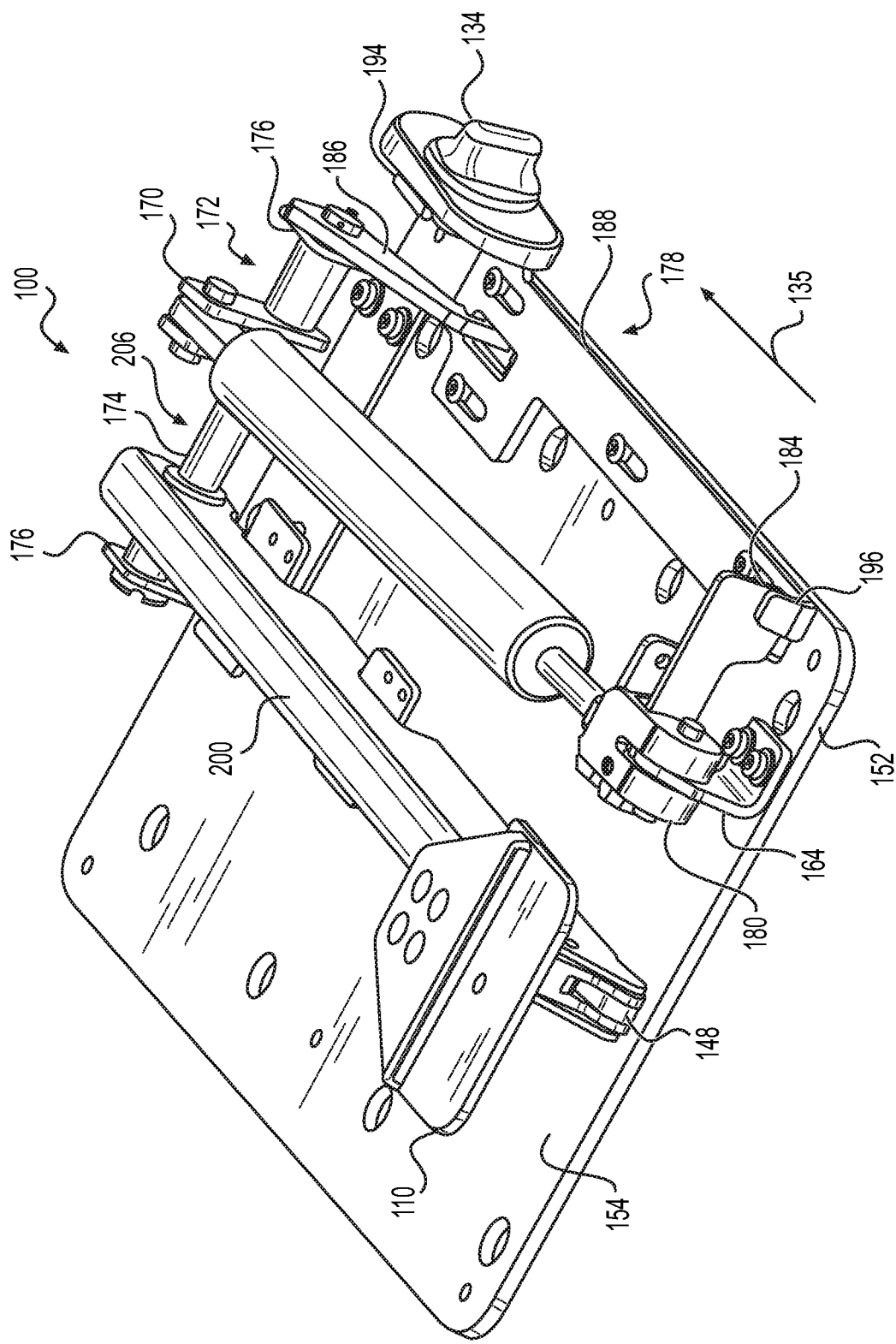
FIG. 6 illustrates another view of the system shown in FIG. 1 with various outer components removed.

As shown in at least FIGS. 5 and 6, in some examples, the system 100 may also include a locking mechanism 178. The locking mechanism 178 may include one or more components configured to assist in fixing the position of, for example, the shaft 174, the drive link 170, the cylinder 159, the housing 161, and/or other movable components of the system 100. For example, such components may be configured to activate, deactivate, energize, deenergize, and/or control the operation of the actuator 158 and/or one or more components thereof. In this way, when the locking mechanism 178 is engaged the position of, for example, the shaft 174, the drive link 170, the cylinder 159, the housing 161, and/or other movable components of the system 100 may be maintained substantially constant. When the locking mechanism 178 is disengaged, however, in some examples, the actuator 158 may be configured to cause rotation and/or other movement of one or more such movable components in response.

For example, in embodiments in which the actuator 158 comprises a gas cylinder, the first end 160 of the actuator 158 may include a housing 180 and/or other similar component that is coupled to the bracket 164 via the joint 166 described above. In such examples, the housing 180 may include, among other things, a relief valve 182 disposed therein, and operably connected to the cylinder 159 and/or the housing 161. When the locking mechanism 178 is engaged, the valve 182 may be configured to remain in a substantially closed position such that pressurized gas disposed within the housing 161, and acting upon the cylinder 159, may remain within a housing 161. It is understood that in the example illustration of FIG. 5, the locking mechanism 178 is engaged and the valve 182 is in the substantially closed position.

In such examples, the system 100 may also include a release arm 184 operably connected to the valve 182. Movement of the release arm 184 in the direction of arrow 135 may cause the valve 182 to at least partially open. Upon at least partially opening, the valve 182 may allow pressurized gas disposed within the house 161 to escape therefrom, and the release of such pressurized gas may cause the actuator 158 to transition from the example retracted state illustrated in FIG. 5 to an example extended state (e.g., the extended state illustrated in FIG. 10 or any other state in which the cylinder 159 is at least partially extended external to the housing 161).

Accordingly, in some examples, the locking mechanism 178 may include a latch 186 and a bracket 188. The latch 186 may comprise a substantially rigid claw, hook, flange, and/or other structure that is rotatable about, for example, the axis 119. In some examples, the latch 186 may be pinned to and/or otherwise fixed to the shaft 174 described above. In such examples, rotation of the shaft 174 may drive and/or otherwise cause commensurate rotation of the latch 186. Alternatively, in further embodiments, the latch 186 may be mounted to a sleeve or other component that is rotatably connected to the shaft 174. In such examples, the shaft 174 may rotate independent of the latch 186, and vice versa. In such examples, the latch 186 may still be rotatable about the axis 119. In still further examples, the latch 186 may be rotatably mounted to the shaft 174 via one or more fittings, bearings, and/or other like components. In any of the examples described herein, when the locking mechanism 178 is engaged, the latch 186 may lockingly engage with the base 152, and/or a component thereof. When the locking mechanism 178 is disengaged, on the other hand, the latch 186 may be rotated about the axis 119, and thus may be disengaged from the base 152.

In any of the examples described herein, the bracket 188 may be slidably and/or otherwise movably connected to the base 152. For example, as shown in FIG. 6, in some embodiments, the bracket 188 may include one or more slots extending substantially, longitudinally along a portion of the bracket 188. In such examples, the system 100 may also include one or more pins extending from the top surface 154 of the base 152. Such pins may extend at least partially within the slots defined by the bracket 188 and may guide movement of the bracket 188 in, for example, the direction of arrow 135 during engagement and/or disengagement of the locking mechanism 178. For example, the bracket 188 may include a first end 190, and a second end 192 opposite the first end 190. In such examples, the second end 192 may include a flange 194 extending therefrom. For example, a central portion of the bracket 188 may extend along the top surface 154, and/or may extend substantially parallel to the top surface 154. In such examples, the central portion of the bracket 188 may comprise a substantially planar surface. Further, in such examples, the flange 194 may extend substantially perpendicularly (relative to the central portion of the bracket 188 and/or relative to the substantially planar surface of the bracket 188) at the second end 192. As shown in at least FIG. 6, the control 134 of the locking mechanism 178 may be connected to the flange 194. Thus, movement of the control 134 (e.g., in the direction of arrow 135) may cause commensurate movement of the bracket 188. The bracket 188 may also include a flange 196 disposed at the first end 190 and at least partially engaged with the release arm 184. Thus, movement of the bracket 188 in the direction of arrow 135 (e.g., caused by movement of the control 134 in the direction of arrow 135) may cause the flange 196 to act upon the release arm 184 two, at least partially open the valve 182. Thus, it is understood that partial opening and/or partial closing of the valve 182 to control the movement and/or location of various movable components of the system 100 may be accomplished by manipulating the control 134.

With continued reference to FIG. 5, the system 100 may also include a support arm 200 disposed opposite the drive link 170. In such examples, the support arm 200 may include a first end 202, and a second end 204 opposite the first end 202. In any of the examples described herein, the support arm 200 may be configured to at least partially support the mount 110, the stem 136, and/or the medical device 102 during use of the system 100. Accordingly, the support arm 200 may comprise any substantially rigid frame, channel, rod, wall, beam, and/or other structure configured to raise and/or lower a medical device 102 mounted to the mount 110 while supporting the entire weight of the medical device 102. Additionally, the support arm 200 may be rotatable about the axis 119 in response to rotation of the shaft 174 and/or movement of the drive link.

For example, the first end 202 of the support arm 200 may be fixed to the shaft 174 via a joint 206, such that rotation of the shaft 174 may cause commensurate rotation of the support arm 200 about the axis 119. In such examples, the joint 206 may be substantially similar to the joint 150 described above. For example, the joint 206 may comprise a substantially fixed joint, or a substantially movable joint. In any such examples, the joint 206 may comprise one or more pins, keys, teeth, fittings, bearings, and/or any other components configured to fixedly connect the support arm 200 to the shaft 174. Additionally, in some examples the axis 119 may extend substantially centrally through the joint 206.

Further, the second end 204 of the support arm 200 may be fixed to the stem 136 via a joint 208. Due to such a configuration, the stem 136 may be at least partially rotatable about the joint 208 as the support arm 200 is caused to rotate about the axis 119 in either the direction of arrow 118 or the direction of arrow 120. In such examples, the joint 208 may be substantially similar to the joint 150 described above. For example, the joint 208 may comprise a substantially fixed joint, or a substantially movable joint. In any such examples, the joint 208 may comprise one or more pins, shafts, keys, teeth, fittings, bearings, and/or any other components configured rotatably connect the stem 136 to the second end 204 of the support arm 200.

As previously mentioned, FIG. 6 illustrates one or more components of the system 100 described above in further detail. In addition, FIGS. 7 and 8 provide different isometric views of various components of the system 100 described herein. For instance, FIG. 7 illustrates a side view of the support arm 200 and other components of the system 100. FIG. 8 provides an additional view of the support arm 200 with a portion removed. As can be seen in at least FIG. 8, in some examples, the timing link 148 described above may extend at least partly within a channel and/or other portion of the support arm 200. In some examples, the timing link 148 may extend substantially centrally through a length of the support arm 200. As described above, the timing link 148 may comprise a substantially rigid beam, rod, shaft, and/or other components of the system 100 configured to assist in maintaining the mount 110 at a substantially constant orientation relative to the base 152 as the support arm 200 transitions between a raised position relative to the base 152 and a lowered position relative to the base 152.

As can be seen in at least FIG. 8, the timing link 148 may include a first end 210 that is configured to pivot, rotate, and/or otherwise move relative to the base 152. In some examples, the first end 210 may be pivotably connected to the base 152. For instance, in such examples, the system 100 may include one or more brackets 214 similar to the bracket 164 described above. In such examples, the first end 210 of the timing link 148 may be pivotably, rotatably, and/or otherwise connected to the bracket 214, such as via one or more joints similar to the joint 166 described above. For example, such a joint may define a substantially central longitudinal axis 216. In such examples, the timing link 148 may be rotatable relative to the base 152 about the axis 21. In such examples, the axis 216 may extend substantially parallel to the axis 119. Alternatively, it is understood that in further examples, the first end 210 of the timing link 148 may be rotatably, pivotably, and/or otherwise connected directly to the base 152, and in such examples, the bracket 214 may be omitted. The timing link 148 may also include a second end 212 opposite the first end 210. As can be seen in FIG. 8, the second end 212 of the timing link 148 may be rotatably, pivotably, and/or otherwise connected to the stem 136 via the joint 150 described above. Additionally or alternatively, the second end 212 of the timing link 148 may be pivotably, rotatably, and/or otherwise connected to the second end 204 of the support arm 200. Further, the mount 110 may be coupled to the second end 212 of the timing link 148 via the stem 136 and the joint 150. Accordingly, it should be understood that the arrangement between the timing link 148, the support arm 200, the actuator 158, and/or the other components of the system 100 described herein may comprise an arrangement similar to a four-bar linkage.

In any of the example embodiments described herein, the system 100 may assist in alleviating physical (e.g., muscle) fatigue caused by lifting, supporting, and/or otherwise maintaining a desired position of the medical device 102 while performing vision screening and/or other medical procedures. For example, the system 100 enables healthcare professionals to temporarily and/or releasably mount a medical device 102, such as a retina screening device, to the mount 110. Once the medical device 102 is mounted to the mount 110, the first portion 114 of the housing 112 may be rotated about the axis 119 by simply moving the control 134 of the locking mechanism 178 in the direction of arrow 135. Manipulating the control 134 this way may cause the valve 182 two at least partially open, thereby releasing pressurized gas from the housing 161 and/or otherwise, at least partly, activating, the actuator 158. Causing the actuator 158 to release pressurized gas in this way may cause the actuator 158 to transition (at least partly) from a retracted state to an extended state. In particular, such a transition may cause the actuator 158 to rotate the drive link 170 about the axis 119. Such rotation may cause the support arm 200 to also rotate about the axis 119, thereby raising the mount 110, and/or the medical device 102, in the direction of arrow 137.

It is understood that due to the configurations described above, a first (e.g., a relatively small) angular rotation of the drive link 170, and/or of the shaft 174 may result in a second angular rotation of the support arm 200 about the axis 119 that is different from (e.g., greater than or less than) the first angular rotation. Additionally, due to the configurations described herein, the orientation of the mount 110 and/or of the medical device 102 mounted thereto, may be maintained substantially constant relative to the support surface 132, the base 152, and/or, other stationary components of the system 110 as the support arm 200 is transitioned between a raised position relative to the base 152 and a lowered position relative to the base 152. Such a substantially constant orientation of the mount 110 is illustrated by comparison of the example raised position of the support arm 200 shown in FIG. 10, and the example lowered position of the support arm 200 shown in FIG. 9. As can be seen in these Figures, a plane A of the mount 110 is maintained substantially parallel to a plane B of the base 152 as the support arm 200 transitions between the example raised position of FIG. 10 and the example lowered position shown in FIG. 9. Moreover, due to the configurations described above, as the actuator 158 acts on the drive link 170 when transitioning from the retracted state to the extended state, the amount of torque and/or force applied to the drive link 170 may decrease. In some examples, the amount of force and/or torque required to lift the medical device 102 connected to the mount 110 may also decrease due to the inherent kinematics of the present system 100.

Other embodiments of the present disclosure will be apparent to those skilled in the art from consideration of the specification and practice of the embodiments described herein. It is intended that the specification and examples be considered as example only, with a true scope and spirit of the present disclosure being indicated by the following claims.

What is claimed is:

1. A system configured to support a medical device, the system comprising:
   a substantially planar base;
   a gas cylinder configured to transition between an extended state and a retracted state, the gas cylinder having a first end connected to a bracket that is fixed relative to the base, and a second end pivotably connected to a drive link;
   a shaft having a longitudinal axis, the shaft being supported by the base and configured to rotate, relative to the base, about the longitudinal axis, the drive link being fixed to the shaft such that movement of the drive link caused by transitioning of the gas cylinder between the extended state and the retracted state results in commensurate rotation of the shaft;
   a support arm disposed opposite the drive link, the support arm having a first end and a second end, the first end of the support arm being fixed to the shaft such that rotation of the shaft causes commensurate rotation of the support arm;
   a timing link having a first end pivotably connected to the base, and a second end disposed opposite the first end of the timing link; and
   a mount coupled to the second end of the timing link, the mount being configured to support the medical device disposed thereon and to maintain a substantially constant orientation relative to the base as the support arm transitions between a raised position relative to the base and a lowered position relative to the base.

2. The system of claim 1, further comprising a housing having a first portion and a second portion, the first portion being moveable between a raised position when the gas cylinder is in the extended state, and a lowered position when the gas cylinder is in the retracted state.

3. The system of claim 1, wherein the mount includes a top surface, a bottom surface, and a spine protruding from the top surface, the spine being configured to mate with a corresponding channel of the medical device when the medical device is disposed on the mount.

4. The system of claim 1, further comprising a locking mechanism configured to releasably fix a position of the shaft about the longitudinal axis.

5. The system of claim 4, wherein the gas cylinder includes a relief valve, and the locking mechanism includes a release arm operably connected to the relief valve, such that movement of the release arm causes the relief valve to at least partially open.

6. The system of claim 5, the locking mechanism further including a latch and a bracket, wherein:
   the latch is fixed to the shaft such that rotation of the shaft about the longitudinal axis causes commensurate rotation of the latch,
   the latch lockingly engages the base to releasably fix the position of the shaft about the longitudinal axis, and
   the bracket is moveable relative to the base to drive movement of the release arm.

7. The system of claim 1, wherein the timing link extends at least partially within a portion of the support arm, the timing link being configured to assist in maintaining the substantially constant orientation of the mount relative to the base as the support arm transitions between the raised position and the lowered position.

8. The system of claim 1, wherein the timing link is rotatable relative to the base about an additional axis, the additional axis extending substantially parallel to the longitudinal axis of the shaft.

9. The system of claim 1, wherein the mount is coupled to the second end of the timing link via a stem extending from the mount to the timing link.

10. The system of claim 9, wherein the stem is pivotably connected to the second end of the timing link via a first joint, and the stem is pivotably connected to the second end of the support arm via a second joint.

11. A system configured to support a device, the system comprising:
    a substantially rigid base having a top surface;
    an actuator connected to the top surface of the base and configured to rotate a drive link about a first longitudinal axis, the first longitudinal axis extending substantially parallel to the top surface;
    a shaft configured to rotate about the first longitudinal axis, the drive link being fixed to the shaft such that movement of the drive link results in commensurate rotation of the shaft;
    a support arm having a first end connected to the shaft, the support arm being rotatable about the first longitudinal axis;
    a substantially rigid timing link having a first end pivotably connected to the base, and a second end disposed opposite the first end of the timing link, the timing link being rotatable, relative to the base, about a second longitudinal axis at the first end of the timing link extending substantially parallel to the first longitudinal axis; and
    a mount coupled to the second end of the timing link, the mount being configured to maintain a substantially constant orientation relative to the base as the support arm transitions between a raised position relative to the base and a lowered position relative to the base.

12. The system of claim 11, wherein the actuator comprises a gas cylinder having a housing and a cylinder extendable from the housing, one of the housing and the cylinder being pivotably connected to the drive link, and the other of the housing and the cylinder being pivotably connected to the base via a bracket that is fixed to the top surface of the base.

13. The system of claim 12, wherein the gas cylinder further includes a relief valve configured to control movement of the cylinder relative to the housing, and
    the system further includes a release arm operably connected to the relief valve such that movement of the release arm causes the relief valve to at least partially open.

14. The system of claim 11, wherein the
    second end of the substantially rigid timing link is pivotably connected to a second end of the support arm, the second end of the support arm being disposed opposite the first end of the support arm.

15. The system of claim 11, wherein the mount is coupled to the second end of the timing link via a stem extending from the mount to the timing link.

16. The system of claim 15, wherein the stem is pivotably connected to the second end of the timing link via a first joint, and the stem is pivotably connected to the second end of the support arm via a second joint.

17. A method of manufacturing a system, the system being configured to support a device, the method comprising:
    providing a substantially rigid base having a top surface;
    pivotably connecting a first end of an actuator to the base via a first bracket fixed to the top surface of the base;
    pivotably connecting a second end of the actuator to a drive link, the drive link being fixed to a shaft such that movement of the drive link results in commensurate rotation of the shaft about a first longitudinal axis, the first longitudinal axis extending substantially parallel to the top surface;

fixing a first end of a support arm to the shaft, the support arm being rotatable about the first longitudinal axis;

pivotably connecting a first end of a substantially rigid timing link to the base, the timing link being rotatable, relative to the base, about a second longitudinal axis at the first end of the timing link extending substantially parallel to the first longitudinal axis; and coupling a mount to a second end of the timing link, opposite the first end of the timing link, via a stem extending from the mount to the second end of the timing link, the mount being configured to maintain a substantially constant orientation relative to the base as the support arm transitions between a raised position relative to the base and a lowered position relative to the base.

18. The method of claim 17, wherein:
the first end of the timing link is pivotably connected to the base via a second bracket fixed to the top surface of the base,
the stem is pivotably connected to the second end of the timing link via a first joint, and the stem is pivotably connected to a second end of the support arm via a second joint.

19. The method of claim 17, wherein the second end of the substantially rigid timing link is pivotably connected to a second end of the support arm, the second end of the support arm being disposed opposite the first end of the support arm.

20. The method of claim 17, further including fixing a latch to the shaft such that rotation of the shaft about the first longitudinal axis causes commensurate rotation of the latch, the latch being configured to lockingly engage the base so as to releasably fix the position of the shaft about the first longitudinal axis.

* * * * *